United States Patent [19]

Cerny et al.

[11] Patent Number: 4,692,452
[45] Date of Patent: Sep. 8, 1987

[54] METHOD FOR TREATMENT OF ENDOMETRITIS IN MAMMALIAN FEMALES

[75] Inventors: Antonin Cerny; Jiri Krepelka; Karel Rezabek; Maria Fruhaufova; Milan Pesak, all of Prague; Bohumil Sevcik; Josef Kral, both of Jilove u Prahy; Antonin Borovicka, Davle; Petr Bilek; Dagmar Picmausova, both of Prague; Josef Stuchlik, Hrabyne; Josef Picha, Jilove u Prahy; Jana Strakova, Prague, all of Czechoslovakia

[73] Assignee: SPOFA, spojene podniky pro zdravotnickou vyrobu, Prague, Czechoslovakia

[21] Appl. No.: 873,616

[22] Filed: Jun. 12, 1986

[30] Foreign Application Priority Data

Jun. 12, 1985 [CS] Czechoslovakia ............... 4246-85

[51] Int. Cl.$^4$ ............................................. A61K 31/44
[52] U.S. Cl. ..................................................... 514/288
[58] Field of Search ......................................... 514/288

[56] References Cited

U.S. PATENT DOCUMENTS

| 3,251,846 | 5/1966 | Semonsky et al. | 514/288 |
| 3,954,988 | 5/1976 | Itil et al. | 514/288 |
| 4,045,562 | 8/1977 | Itil et al. | 514/288 |
| 4,096,266 | 6/1978 | Itil | 514/288 |
| 4,379,790 | 4/1983 | Hotowski et al. | 514/288 |
| 4,522,820 | 6/1985 | Dorow et al. | 514/288 |
| 4,593,032 | 6/1986 | Kehr et al. | 514/288 |

FOREIGN PATENT DOCUMENTS

| 0615929 | 2/1980 | Czechoslovakia . | |
| 0622518 | 4/1981 | Czechoslovakia . | |
| 2523026 | 12/1976 | Fed. Rep. of Germany | 514/288 |
| 3,410,218 | 9/1985 | Fed. Rep. of Germany | 514/288 |
| 950528 | 2/1964 | United Kingdom . | |
| 1174617 | 12/1969 | United Kingdom . | |
| 2116548 | 9/1983 | United Kingdom | 514/288 |

OTHER PUBLICATIONS

Cerny et al., Collection Czechoslovak Chem. Commun., vol. 49, pp. 2828–2836 (1984).

Primary Examiner—Jerome D. Goldberg
Assistant Examiner—Y. Krosnick

[57] ABSTRACT

This invention relates to a method for the treatment of endometritis (chronic and/or acute puerperal inflammations) in mammalian females comprising the administration of 1-(8-alpha-ergolinyl)-3,3-diethylurea derivatives of Formula I

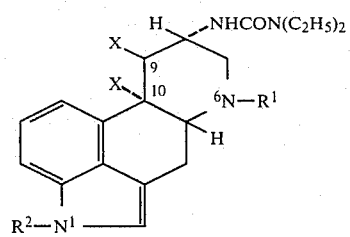

in which $R^1$ represents an alkyl group containing 1 to 3 carbon atoms, $R^2$ represents a hydrogen atom or an alkyl group containing 1 to 3 carbon atoms, and X represents a hydrogen atom or a double bond between the carbon atoms at positions 9 and 10. The compound according to Formula I, or a pharmaceutically acceptable acid addition salt thereof, is the physiologically active component of the therapeutic composition and method. The compound may be combined with a pharmaceutically acceptable diluent, vehicle, excipient, auxiliary, or carrier. The invention is particularly advantageous in veterinary medicine, when applied to the treatment of farm animals, such a cows.

6 Claims, No Drawings

METHOD FOR TREATMENT OF ENDOMETRITIS IN MAMMALIAN FEMALES

This invention relates to a method for the treatment of chronic and acute puerperal endometritis in mammalian females comprising the administration of 1-(8-alpha-ergolinyl)-3,3-diethylurea derivatives of Formula I

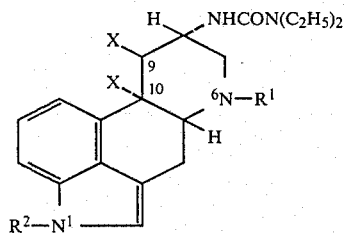

in which $R^1$ represents an alkyl group containing 1 to 3 carbon atoms, $R^2$ represents a hydrogen atom or an alkyl group containing 1 to 3 carbon atoms, and X represents a hydrogen atom or a double bond between the carbon atoms at positions 9 and 10. The compound according to Formula I, or a pharmaceutically acceptable acid addition salt thereof, is the physiologically active component of the therapeutic composition and method. The compound may be combined with a pharmaceutically acceptable

BACKGROUND OF THE INVENTION

Acute puerperal endometrial inflammations and chronic endometrial inflammations (endometritis) are very common in female farm animals, especially cows. Approximately 10 to 20 percent of calved animals are affected by these diseases, and the affected animals suffer temporary sterility. In severe cases, sterility can be permanent. The contemporary treatment of endometritis in farm animals comprises the intrauterine administration of antibiotics, chemotherapy, and/or disinfectants, sometimes supplemented with parenteral uterotonic medication. Acute and chronic endometritis are also relatively common illnesses in women.

It has been discovered that, unexpectedly, the compounds of Formula I can be advantageously applied to endometritis therapy in mammalian females. Compounds of Formula I and different methods for their preparation have been reported in Czechoslovak Author Certificates Nos. 100,832; 152,153; 156,178; and 217,941. See also, Cerny et al., applicants' commonly owned copending application, Ser. No. 676,060 and British Published Application No. 2,116,548. The known compounds, teruguride, lisuride, and proteguride, have been disclosed as useful with respect to dopaminergic action, inhibition of prolactin and growth hormone, stimulation of gonadotropins and antiserotonin activity. The compounds of Formula I have not heretofore been suggested or disclosed as useful for the treatment of endometritis.

SUMMARY OF THE INVENTION

The treatment of acute puerperal and chronic inflammations according to the invention is based on the unexpected action of the ergoline derivatives of Formula I on the endocrine regulatory system controlling the female genital tract. The administration of these compounds elicits substantial changes in the intrauterine secretion and in the intraluminal content of the uterine cavity. This results in suppression of the endometrial inflammation without administration of antibacterial agents.

The treatment according to the invention has been tested and verified in females of several mammalian species. Experiments have shown that the administration of terguride, 1[(5R,8S,10R)-6-methyl-8-ergolinyl]-3,3-diethylurea, a typical compound of the invention having the Formula II:

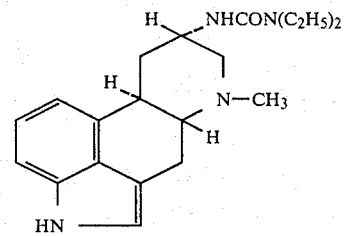

to healthy rats provokes a surprising stimulation of the estrogenic hormones present in the organism in the intrauterine milieu and the vaginal epithelium. The effect of teguride on the epithelial tissue was shown microscopically, upon examination of vaginal smears. Disappearance of leucocytes, keratinization of epithelial cells, a pronounced increase in the lactobacilli count, and decrease of the intravaginal pH to values under 5.5 are observed. The effect of the compound on the intrauterine milieu was shown by increased secretion of the limpid, chlorides intrauterine fluid, which physiologically enables penetration of spermatozoa and transport of ova during the ovulation period. All of these changes, including an increase in the chloride content of the uterine liquor, create conditions which discourage bacterial infection and suppress the proliferation of pathogenic microorganisms in the genital tract of mammalian females.

DETAILED DESCRIPTION

The effect of teguride on vaginal cytology in healthy adult female rats was studied primarily according to two experiments, as described in detail below. Additional tests on female cows suffering from endomitritis demonstrate, as explained below, that the treatment according to the invention is safe and effective when administered to farm animals for the treatment of endometritis according to the dosages disclosed. These examples and experiments are, of course, representative, and do not serve to limit the scope of the invention or the appended claims.

EXPERIMENT 1

The first experiment was concerned with the effect of shortterm administration of terguride upon the action of estradiol on the quantity of intraluminal uterine fluid and on the maturation of vaginary epithelial cells. Administration of the compound resulted in a markedly pronounced enhancement of the estrogenic effect. A first group of six animals was given 0.05 mg/kg of estradiol valerate (Neofollin, Spofa) s.c. on day 1 of the assay. A second group of six animals was similarly medicated and received 1 mg/kg of terguride p.o. twice daily on days 1 and 2. A third group of six animals was the control, and remained untreated. On day 3 the animals were sacrificed and examined. Assay results are set forth in Table I, which demonstrates that the effects of a low dose of estrogen on the vaginal epithelium and intrauterine fluid were very markedly promoted by the simultaneous administration of terguride.

EXPERIMENT 2

In the second experiment, the long-term effects of terguride administration on the action of estradiol valerate and endogenous estrogens on the vaginal epithelium and intrauterine fluid were studied at different dosage levels. The experiment was conducted for 20 days, and each experimental group contained six normal adult female rats. The first group was given 1.25 mg/kg of estradiol valerate (Neofollin, Spofa) s.c. twice weekly at intervals of 3 to 4 days over the 20 day period. The second group received 5 mg/kg of terguride p.o. once daily. A third group received 1.25 mg/kg of estradiol valerate s.c. twice weekly at intervals of 3 or 4 days and 0.5 mg/kg p.o. of terguride once daily. A fourth group received 1.25 mg/kg of estradiol valerate s.c. twice weekly at intervals of 3 or 4 days and 5 mg/kg p.o. of terguride once daily. A fifth control group was untreated.

The animals were sacrificed and examined on day 21. The results of the examination and assay are summarized in Table II, which demonstrates that the pure estrogenic effect of estradiol on the sexual organs of females—undisturbed by the action of progesterone, the secretion of which is augmented by the administration of an estrogen in adult females—was only achieved when estradiol valerate was combined with terguride. When administered alone, terguride significantly promoted the estrogenic action of endogenous estrogens.

EXPERIMENT 3

Female cows suffering from endometritis, 118 in number, were given a composition containing 20.0 mg of terguride dihydrogen citrate in 5.0 ml of isotonic saline solution. Some of the cows were previously untreated, while others had received local antibiotic treatment. The pathological condition of the uterus of the treated animals was characterized as (a) puerperal catarrhal to necrotic inflammation with an atonic enlarged uterus charged with secretions, or (b) chronic inflammation with a copious mucopurulent discharge. Pyometra was diagnosed in 19 cows. Uterine cervical smears were examined and were found to contain *Staphylococcus pyogenes, Escherichia coli, Proteus vulgaris* and *Streptococcus viridans*. The medicinal composition according to the invention was injected into the gluteus muscle, and the animals were examined for the next six days.

Pathological uterine symptoms completely disappeared in 64 animals (54.2%) and were markedly moderated in 18 animals (15.3%). In 36 animals (30.5%) the disease was substantially unchanged. The treatment was repeated in the symptomatic animals, which were examined for another 5 days. After a single or double treatment, as needed and according to the invention, endometritic symptoms disappeared completely in 83 cows (70.3%), pronounced amelioration of symptoms was observed in 16 cows (13.5%), and the disease remained unchanged in only 19 cows (16.2%). These results were achieved within 10–11 days after the start of treatment.

TABLE I

| GROUP | Avg. Volume of Intrauterine fluid | Keratinization | Lactobacilli |
|---|---|---|---|
| Control | 0.04 ml | 3 (50%) | 1 (17%) |
| Estradiol valerate | 0.09 ml | 1 (17%) | 2 (33%) |
| Estradiol valerate and terguride | 0.42 ml | 6 (100%) | 5 (83%) |

TABLE II

| GROUP | Avg. Vol. of uterine fluid | Leukocytes | Keratinization | Lactobacilli |
|---|---|---|---|---|
| Control | 0.05 ml | 3 (50%) | 1 (17%) | 0 |
| Estradiol valerate | 2.3 ml | 6 (100%) | 0 | 0 |
| Terguride | 0.4 ml | 1 (17%) | 5 (83%) | 1 (17%) |
| Estradiol valerate and terguride (0.5 mg/kg daily) | 4.8 ml | 1 (17%) | 4 (67%) | 5 (83%) |
| Estradiol valerate and terguride (5.0 mg/kg daily) | 5.4 ml | 0 | 6 (100%) | 6 (100%) |

1. Positive findings in the control group are due to the occurence of spontaneous cyclic estrus or proestrus.
2. The dosage schedule is provided at page 6–7, infra.
3. The leukocyte, keratinization, and lactobacilli data refers to the number of animals showing positive with an intravaginal massive occurrence as evaluated microscopically from a smear, with leukocytes indicating an absence of a substantial estrogenic stimulation, keratinization referring to predominantly keratinized epithelial cells (a symptom of estrogenic stimulation), and lactobacilli indicating a eubiotic state (i.e., the absence of inflamation producing bacteria.

The main advantage of the treatment and composition according to the invention, when compared to known methods of veterinary endometritic therapy, is a dramatic reduction in the time required for treatment. Intrauterine antibiotic therapy generally requires a 15 to 30 day treatment period. The present invention achieves the same therapeutic results in 5 to 10 days. An additional advantage of the invention resides in its easy single or double parenteral administration, without any need to restrain the animals. The traditional intrauterine antibiotic medication requires the assistance of auxiliary personal to restrain the animals and the treatment must be repeated several times. Yet another advantage of the invention-resides in its ability to combat endometritis by providing a natural uterine environment that is unsuitable to the disease, and within which the harmful pathogens cannot survive. Known methods rely on antibiotics to destroy the pathogenic microorganism, and this can cause side effects or contraindications which do not apply to the treatment according to the invention.

The method of treatment according to the invention comprises the administration of a compound of Formula I, preferably terguride, in the form of its base or as an acid addition salt in combination with a pharmaceutically acceptable organic or inorganic acid.

The following compounds are exemplary embodiments of the compounds administered according to the method of the invention:
1. Terguride, 1-(5R,8S,10R)-6-methyl-8-ergolinyl)-3,3-diethylurea, see Formula II.
2. Lisuride, 1-(5R,8S)-6-methyl-9,10-dihydro-8-ergolinyl)-3,3-diethyl-urea, wherein $R^1$ is a methyl group, $R^2$ is a hydrogen atom, and the Xs represent a double bond between the carbon atoms at positions 9 and 10 of Formula I.

3. Proterguride, 1-(5R,8S,10R)-6-propyl-8-ergolinyl)-3,3-diethylurea, wherein according to Formula I, $R^1$ is a propyl group, and $R^2$ and each X represent a hydrogen atom.
4. 1-(5R,8S,10R)-1-methyl-6-propyl-8-ergolinyl)-3,3-diethylurea, wherein according to Formula I, $R^1$ is a propyl group, $R^2$ represents a methyl group, and each X represent a hydrogen atom.

Suitable inorganic acids for the preparation of water-soluble addition salts of the compounds of Formula I are hydrochloric, hydrobromic and phosphoric acid. Suitable organic acids for the same purpose are acetic, maleic, tartaric, citric, terebic, and methanesulfonic. The compound can be administered orally, parenterally, or transdermally.

Oral administration can be advantageously achieved by providing the active compound of Formula I in the form of capsules, tablets, pellets, granules, powders, solutions, or premixes prepared according to known and accepted pharmaceutical methods. Common solvents, diluents, vehicles, and/or auxiliary carriers can be used, such as talcum, starches, sugars, cellulose derivatives, artificial flavors, and stabilizers.

Parenteral administration can be achieved by subcutaneous, intramuscular or intravenous injection. For preparation of a solution suitable for injection, a compound of Formula I, preferably in the form of an acid addition salt, is dissolved in a convenient inert solvent, such as distilled water, an isotonic sodium chloride solution, or an aqueous glucose solution. If desired, known stabilizers and/or solubilizers can be conveniently added. The solution is sterilized by filtration with inert microporous materials, is dosed into ampoules, and the ampoules are freeze-dried. Alternatively, parenteral administration can be achieved by injecting an oily solution or suspension of the active ingredient.

Transdermal administration of the compounds of Formula I can be achieved through the application of ointments, cremes or solutions prepared by combining a compound of Formula I with known carriers according to known methods.

The appropriate dosage is dependent on the specific compound of Formula I that is chosen, and on the means of administration, the nature and severity of the disease, and the particular species and animal being treated. The precise dosage chosen for each individual administration must be determined by a skilled medical or veterinary practicioner. Cows suffering from endometritis are usually treated with a single intramuscular injection containing 20 mg of the dihydrogen-citrate salt of terguride, or approximately 0.05 mg of the said i.m. per kg of weight. If necessary, the treatment is repeated at the same dosage after 2 to 10 days.

The dosage forms and treatment regimens contemplated by the invention are further illustrated by a number of examples which focus on terguride, one of the compounds of Formula I. The other compounds of Formula I can be prepared and administered in a similar manner. The examples do not serve to limit the scope of the disclosure or the appended claims.

EXAMPLE 1

Liquid Parenteral Injection terguride (dihydrogen citrate): 2.0 g
sodium chloride: 4.2 g
distilled water: up to 500.0 ml A solution is prepared at room temperature by mixing 2.0 g terguride, in its dihydrogen-citrate addition salt form, with an aqueous sodium chloride solution containing 4.2 g of sodium chloride, with stirring and the addition of distilled water, to obtain a final solution volume of 500.0 ml. The solution is sterilized by microporous filtration and is dosed into 5.0 ml ampoules.

EXAMPLE 2

Dry Injections (freeze dried)

terguride (dihydrogen citrate): 1.2 g
sodium hydrogencarbonate: q.s. (to pH 3.0–3.5)
low mol. wt. dextrane: 15.0 g
distilled water: up to 300.0 ml Citric acid is dissolved in distilled water and the solution is adjusted by gradual addition of sodium hydrogencarbonate to a pH of 3.0 to 3.5. The terguride dihydrogen citrate and dextrane are dissolved in the obtained medium and the solution is diluted with distilled water to a final volume of 300 ml. The solution is sterilized by filtration, is dosed into 5.0 ml vials and is freeze-dried. Immediately before application, the dry solid is dissolved in 5 ml of a sterile isotonic aqueous sodium chloride solution.

EXAMPLE 3

Tablets terguride (hydrogenmaleate): 0.5 g
lactose: 144.5 g
calcium hydrogenphosphate dihydrate: 97.0 g
maize starch: 180.0 g
microcrystalline cellulose: 60.0 g
calcium stearate: 18.0 g The active component is mixed successively with each of the above inactive or auxiliary components, and the final mixture is thoroughly homogenized and pressed on a rotary tabletting machine to obtain 500 mg tablets, each of which is 13 mm in diameter and contains 0.5 mg of the active compound.

We claim:
1. A method for the treatment of endometritis in mammalian females in need of said treatment comprising the administration to said mammalian female of an effective amount for treating endometritis of 1-(8-alpha-ergolinyl)-3,3-diethylurea derivative or a pharmaceutically acceptable acid addition salt thereof of Formula I

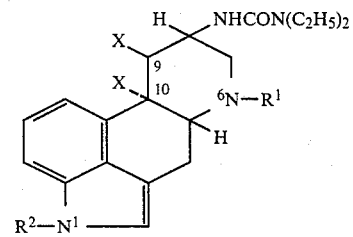

wherein $R^1$ is alkyl having from 1 to 3 carbon atoms, $R^2$ is selected from the group consisting of hydrogen and alkyl having 1 to 3 carbon atoms, and X is selected from the group consisting of hydrogen and a double bond between the carbon atoms at positions 9 and 10.

2. A method for the treatment of endometritis in mammalian females in need of said treatment comprising the administration to said mammalian female of an effective amount for treating endometritis of a compound selected from the group consisting of
- 1-[(5R,8S,10R)-6-methyl-8-ergolinyl]-3,3-diethylurea,
- 1-(5R,8S)-6-methyl-9,10-dihydro-8-ergolinyl)-3,3-diethylurea,
- 1-(5R,8S,10R)-6-propyl-8-ergolinyl)-3,3-diethylurea, and
- 1-(5R,8S,10R)-1-methyl-6-propyl-8-ergolinyl)-3,3-diethylurea or a pharmaceutically acceptable acid addition salt thereof.

3. A method according to claim 1 wherein the compound according to Formula I is administered in the form of a pharmaceutically acceptable acid addition salt, with the acid selected from the group consisting of hydrochloric, hydrobromic, phosphoric, acetic, maleic, tartaric, citric, terebic, and methanesulfonic acid.

4. A method according to claim 2 wherein the compound is administered in the form of a pharmaceutically acceptable acid addition salt, with the acid selected from the group consisting of hydrochloric, hydrobromic, phosphoric, acetic, maleic, tartaric, citric, terebic, and methanesulfonic acid.

5. A method for the treatment of endometritis in mammalian females in need of said treatment comprising the administration to said mammalian female of about 0.05 mg/kg of a 1-(8-alpha-ergolinyl)-3,3-diethylurea derivative of Formula I

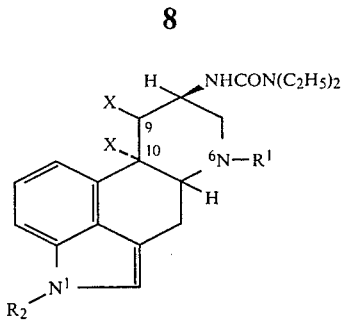

wherein $R^1$ is alkyl having from 1 to 3 carbon atoms, $R^2$ is selected from the group consisting of hydrogen and alkyl having 1 to 3 carbon atoms, and X is selected from the group consisting of hydrogen and a double bond between the carbon atoms at positions 9 and 10,
said derivative being administered in the form of an acid addition salt with an acid selected from the group consisting of hydrochloric, hydrobromic, phosphoric, acetic, maleic, tartaric, citric, terebic, and methanesulfonic acid.

6. A method for the treatment of endometritis in mammalian females in need of said treatment comprising the steps of administering to said mammalian female a first dose of a solution containing 20 mg of 1-(5R,8S,10R)-6-methyl-8-ergolinyl)-3,3-diethylurea dihydrogen citrate by intramuscular injection, and administering to said mammalian female a second identical dose within from 2 to 10 days following the first administration, as needed.

* * * * *